United States Patent

Heimberger et al.

[11] Patent Number: 5,919,205
[45] Date of Patent: Jul. 6, 1999

[54] OPERATING ROD FOR A MEDICAL INSTRUMENT, IN PARTICULAR FOR AN ENDOSCOPIC INSTRUMENT

[75] Inventors: Rudolf Heimberger, Oberderdingen; Uwe Schaumann, Villingen-Schwenningen, both of Germany

[73] Assignee: Richard Wolf GmbH, Knittlingen, Germany

[21] Appl. No.: 08/926,398

[22] Filed: Sep. 9, 1997

[30] Foreign Application Priority Data

Sep. 12, 1996 [DE] Germany ............... 196 36 976

[51] Int. Cl.$^6$ ............................................. A61B 17/28
[52] U.S. Cl. ....................................... 606/205; 60/167
[58] Field of Search ............................. 606/205, 167; 403/341

[56] References Cited

U.S. PATENT DOCUMENTS

| | | |
|---|---|---|
| 709,400 | 9/1902 | Fitzpatrick ............................ 403/341 |
| 867,312 | 10/1907 | Shutz . |
| 1,003,973 | 9/1911 | Barrickman . |
| 3,220,757 | 11/1965 | Potter . |
| 5,439,309 | 8/1995 | Raz . |
| 5,792,165 | 8/1998 | Klieman et al. .................... 606/205 |

FOREIGN PATENT DOCUMENTS 43 13 903 C1  9/1994  Germany .

*Primary Examiner*—Michael Buiz
*Assistant Examiner*—Jackie Tan-Uyen T. Ho
*Attorney, Agent, or Firm*—Panitch Schwarze Jacobs & Nadel, P.C.

[57] ABSTRACT

The operating rod is provided for a medical instrument, in particular for an endoscopic instrument and consists of at least two rod parts transmitting tension and/or compression forces and which at their ends facing one another, are connected to one another with a positive fit at least in the direction of their longitudinal axis. In order to achieve a high force transmission with a slimline construction, the face ends facing one another, of the rod parts are arranged essentially in a plane lying obliquely to the longitudinal axis of the rod and are provided with toothed profiles engaging into one another with a positive fit.

11 Claims, 1 Drawing Sheet

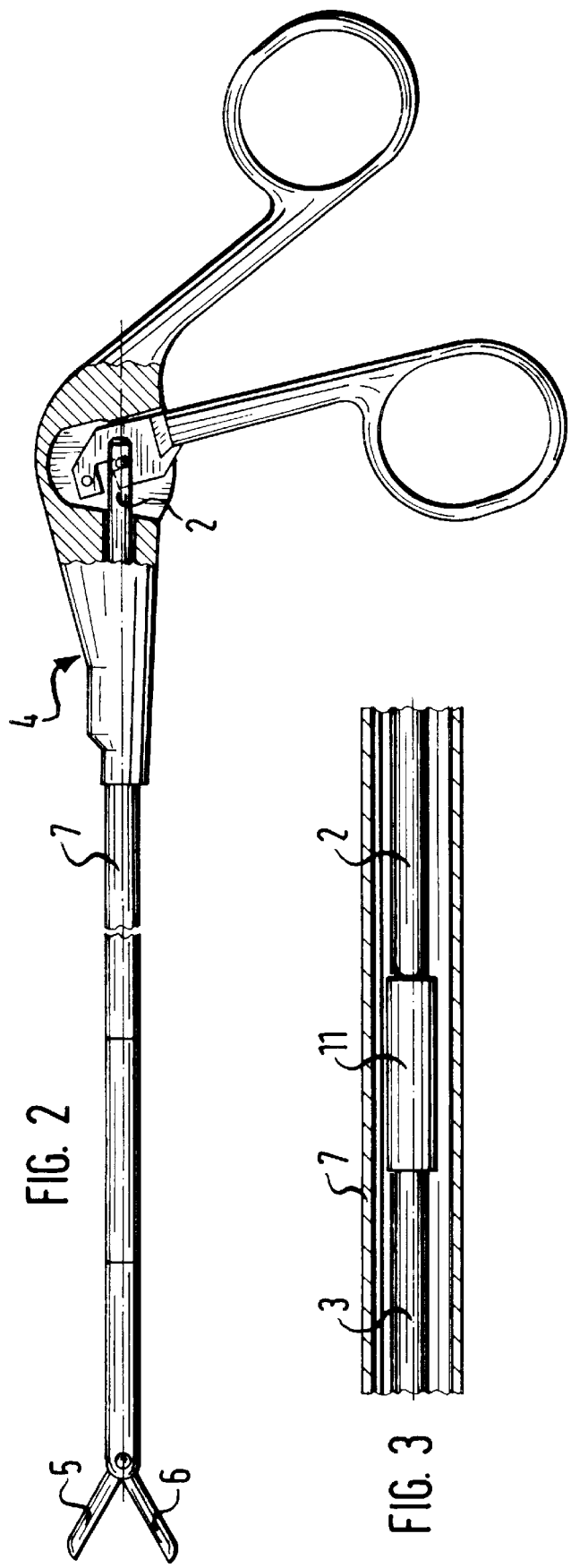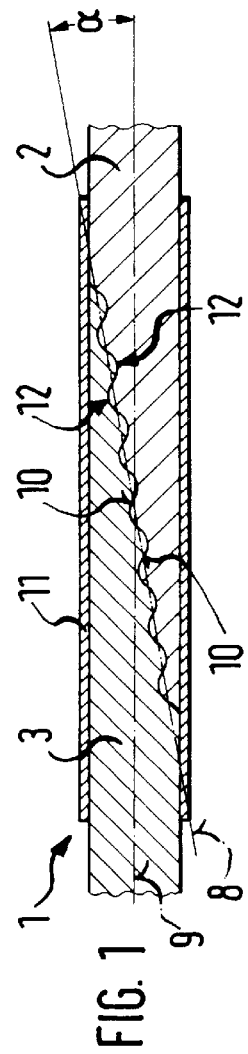

OPERATING ROD FOR A MEDICAL INSTRUMENT, IN PARTICULAR FOR AN ENDOSCOPIC INSTRUMENT

BACKGROUND OF THE INVENTION

The invention relates to an operating rod for a medical instrument, in particular for an endoscopic instrument which comprises at least two rod parts transmitting tension and/or compression forces and which at their ends facing one another are connected to one another with a positive fit at least in the direction of their longitudinal axis.

Operating rods of this type which for example are applied in endoscopic forceps, transmit tension and compression forces from a handle arranged on the proximal side onto a tool arranged on the distal side, for example the jaw parts of an endoscopic forceps. Due to reasons of hygiene it is often desirable to construct the instrument from several parts so that it can be quickly and simply dismantled for cleaning purposes and later can be put back together again. A multi-part construction is particularly problematic with the operating rod which as a rule is guided within a shank, since the known positive fit connections for this in the form of the usual threaded connections either extends radially projecting or also considerably reduce the effective cross section of the operating rod which is further reduced in practice by the notch effect caused by the fitting of the thread. In particular, with thin operating rods there are at present no known suitable positive fit connections, so that as a rule, one must fall back on material fit connections, that is welding or adhesing. The adhesive connections can be generally neglected since the necessary stability cannot often be guaranteed in particular after repeated sterilization treatment. With welding and soldering connections there then arise problems when materials are used which are not connectable to one another or only with great difficulty, for example stainless steel on the one hand and on the other hand a nickel titanium alloy (memory metal), or for example steel and plastic.

From U.S. Pat. No. 3,220,757 as well as U.S. Pat. No. 5,439,309, positive fit connections of the most general type are known, these being formed by toothed profiles engaging into one another. The positive fit connections disclosed here can also for example be applied to rods, wherein a spring pretensioned cap is provided which secures the toothed profiles in the radial direction with a positive fit. This radial, comparatively bulky cap is not suitable for the connection of slim endoscopic instruments. The positive fit connections described are also quite unstable. Due to the profiled arrangement in the region of the longitudinal center axis, there results a reduction of the effective rod cross section of about one half. Furthermore by way of the toothing arrangement transverse to the longitudinal axis there is a high notch effect. The positive fit connections described are therefore not very suitable for application as an operating rod for an endoscopic instrument.

BRIEF SUMMARY OF THE INVENTION

Proceeding from this it is the object of the invention to provide an operating rod which is constructed of several parts and where appropriate of different materials, and which has at the same time small radial dimensions and which can transmit high tension and/or compression forces. The operating rod should furthermore be inexpensive and simple to manufacture and assemble.

According to the invention, this object is achieved in a medical instrument described at the outset, wherein the face ends of the rod parts which face one another lie obliquely to the longitudinal axis and are provided with toothed profiles engaging into one another with a positive fit.

Accordingly, the invention provides for the face ends of the rod parts to be skewed and to be provided with a toothed profile so that the partition plane does not run transversely to the longitudinal axis as is usual with threaded connections, but obliquely to the longitudinal axis of the operating rod. The toothing of the profiles is preferably formed and arranged such that their elevations are directed essentially transversely to an oblique plane. With a suitable choice of angle of the oblique plane—this should be as flat as possible—as well as of the toothed profile, with this positive fit connection, particularly also tension forces, corresponding to those able to be transmitted with a complete shank cross section, may be transmitted in the longitudinal direction of the operating rod. With the positive fit connection according to the invention therefore, with a comparatively small cross section, much higher forces can be transmitted than with those of U.S. Pat. No. 3,220,757 or U.S. Pat. No. 5,439,309.

If the operating rod, as is usual with endoscopic instruments, is guided axially movable within the shank with only a small amount of play, then the shank can form the securing of the positive fit connection in the radial direction, that is to the longitudinal axis, so that on removing the operating rod from the shank, the operating rod can be broken up into its rod parts.

When however it is a case not of the ability to dismantle but merely of the connectability of different materials given a small outer diameter, then it may be useful to cover over the region of these oblique overlapping face ends, provided with a toothed profile, with a casing tube which surrounds the rod parts in this region as play-free as possible. When the ability to release the connection is not important, this casing tube is advantageously fastened on the operating rod by adhesing. This adhesive connection covers a large surface and in practice is hardly loaded so that the sterilization procedures which are otherwise damaging to the adhesive connection have practically no effect. For levelling the peak loads moreover, the toothed profiles may additionally be connected to one another by adhesing.

The profiles themselves may for example be formed wave-shaped or saw-tooth-shaped. A steeper design of the tooth profile flanks would as a rule be chosen when the rod parts are secured in the radial direction by a shank with some play, even if this is slight. The steeper and higher the profile flanks, the larger becomes the allowable radial play of the surrounding guide and the smaller are the forces which can be transmitted in the direction of the longitudinal axis of the shank. Vice-versa therefore, flat wave-shaped profiles are to be preferred with the embodiments, with which the connection region of the rod parts is surrounded by a casing tube as play-free as possible. Then particularly high forces can be transmitted.

The angle of the partition plane, that is the oblique plane in which the toothed profiles are arranged, is to lie between 10° and 40° to the longitudinal axis of the operating rod, preferably approximately in a region of 15° thereto.

It is particularly advantageous when the toothed profiles of the one and of the other rod part are formed the same since these may then be manufactured with the same machine without having to adjust the latter.

The positive fit connection according to the invention is preferably suitable for operating rods with a small diameter, in particular with a diameter between 0.5 mm and 1 mm, since up to now there has been no alternative positive fit connection for these diameter regions.

A prefered application of the invention lies in being able to assemble the operating rod from rod parts of differing material. Thus for example an operating rod may consist of three rod parts, wherein the rod parts on the end sides are as usual composed of stainless steel and the rod part incorporated therebetween is composed of nickel titanium alloy. In this manner, an overload safety device may be integrated into the operating rod without having to noticeably increase the diameter or having to adapt the end side materials thereto. In this context the document DE-A-4 313 903 is referred to.

BRIEF DESCRIPTION OF THE DRAWINGS

The invention is hereinafter decribed by way of an embodiment example shown in the drawings. There is shown:

FIG. 1: in a longitudinal section, the connection region of two rod parts of the operating rod according to the invention, FIG. 2: in a schematic representation, an endoscopic forceps in a lateral view and a part section and FIG. 3: in an enlarged representation, a section through the forceps shank in the region of the connection of the rod parts of the operating rod.

DETAILED DESCRIPTION OF THE INVENTION

In FIG. 1 there is shown an operating rod 1 according to the invention which consists of two rod parts 2 and 3. The operating rod 1 is arranged within an endoscopic instrument 4 shown in FIG. 2. With the endoscopic instrument represented in FIG. 2 it is the case of a forceps which is provided with an operating rod 1 for operating distally arranged jaw parts 5, 6. This operating rod 1, in the direction of its longitudinal axis 9, is displaceably guided in the shank 7 of the endoscopic instrument 4 so that on operating the proximal handle part, the jaw parts 5 and 6 are moved in that the operating rod 1 is displaced within the shank.

The forces acting upon the rod part 2 on operation of the endoscopic instrument 4 are transmitted by the rod part 3 which is in a positive fit engagement with this rod part and which is connected to the jaw parts 5 and 6 in the known pivotably movable manner.

The connection of the rod parts 2 and 3 is effected via toothed profiles 10 which engage into one another and which are provided on end faces, facing one another and arranged obliquely to the longitudinal axis 9, of the rod parts 2 and 3. With the embodiment form represented, the profiles are wave-shaped, so that in the longitudinal section they run approximately sinusoidally. The end faces, facing one another and comprising the toothed profiles 10 lie essentially in a plane 8 which is arranged at an acute angle α of 15° to the longitudinal axis 9. The toothed profiles are so formed that an elevation 12 engages flush in the indentation of the counter profile lying opposite. Instead of the wave-shaped profiling, a profiling similar to a saw-tooth or another suitable profile may be provided. According to the profiled toothing employed, where appropriate the angle α is also to be adapted.

Since the flanks of each elevation 12 are directed obliquely to the longitudinal axis 9 of the operating rod 1, in a case of loading (compression or tension force in the direction of the longitudinal axis 9), there results also a tranverse force which is directed essentially radially to the longitudinal axis 9. In order to prevent the rod parts on account of this transverse force, from drifting radially away from one another and thus from also losing their positive fit in the axial direction, the operating rod 1, at least in the region of the separation plane 8 must be secured against radial slippage. This may be effected by the shank in that the rod 1 is guided, or also as with the embodiment form represented, by a casing tube 11 which surrounds the rod parts 2 and 3 in the region of this positive fit connection lying as tightly as possible. It can be deduced from FIG. 3 how this positive fit connection secured with this casing tube 11 lies within the instrument shank 7 with play.

This in turn means that as a rule, in the region of the positive fit connection of the rod parts 2 and 3 there is no frictional engagement between the operating rod and the casing tube 11, which is why the casing tube is here connected to the operating rod by adhesing. This large surfaced adhesing serves merely for fixing the casing tube on the desired location of the tension rod 1. Moreover, with a suitable choice of adhesive (hot-melt-type adhesive, adhesive which can be attacked with solvent), the casing tube 11 when required may be removed by loosening the adhesive and undoing the positive fit between the rod parts.

With the embodiment form represented, as can be deduced from FIG. 1, the toothed profile of both rod parts 2 and 3 is formed identically. The rod parts 2 and 3 are arranged rotated about 180° to one another, wherein both toothed profiles flushly engage into one another with a positive fit. In this manner, the toothed profiles may be manufactured with the same machine on the same basic setting.

We claim:

1. An endoscopic instrument comprising:
an operating rod having a longitudinal axis, said operating rod being made of two parts; each of said two rod parts having first and second end faces, said first end face of said first rod part being connected to a handle, said first end of said second rod part being connected to a tool, said second end faces of the two rod parts being provided with a toothed profile which lies in an oblique plane to the longitudinal axis of said operating rod, said two rod parts being connected to one another at said second end faces by said toothed profiles engaging one another with a positive fit such that said two rod parts transmit tension and/or compression forces between said handle and said tool.

2. An endoscopic instrument rod according to claim 1, wherein the elevations of the toothed profile are directed essentially transversely to a plane which lies obliquely to the longitudinal axis.

3. An endoscopic instrument rod according to claim 1, wherein the oblique plane has an angle α of 10° to 40°, preferably about 15° to the longitudinal axis of the operating rod.

4. An endoscopic instrument rod according to claim 1, wherein the toothed profiles provided on the face ends, of the rod parts, which face one another, are wave-shaped.

5. An endoscopic instrument rod according to claim 1, wherein the toothed profiles provided on the face ends, of the rod parts, which face one another, are saw-tooth-shaped.

6. An endoscopic instrument rod according to claim 1, wherein the toothed profiles provided on the ends, of the rod parts, which face one another, are formed the same.

7. An endoscopic instrument rod according to claim 1, wherein the toothed profiles provided on the ends, of the rod parts, which facing one another, are formed complementary to one another.

8. An endoscopic instrument rod according to claim 1, wherein the rod parts in the region of the toothed profiles are surrounded by a casing tube.

9. An endoscopic instrument rod according to claim 8, wherein the casing tube is connected to the rod parts by adhesing.

10. An endoscopic instrument rod according to claim 1, wherein the rod parts are connected to one another in the region of their toothed profiles by adhesing.

11. An endoscopic instrument rod according to claim 1, wherein the rod parts have a diameter of 0.5 mm to 1 mm.

* * * * *